(12) United States Patent
Bunyard et al.

(10) Patent No.: US 8,133,825 B2
(45) Date of Patent: *Mar. 13, 2012

(54) DISPERSIBLE WET WIPES

(75) Inventors: W. Clayton Bunyard, DePere, WI (US); Michael Ralph Lostocco, Appleton, WI (US); Kelly Dean Branham, Woodstock, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 856 days.

This patent is subject to a terminal disclaimer.

(21) Appl. No.: 11/413,446

(22) Filed: Apr. 28, 2006

(65) Prior Publication Data

US 2007/0254543 A1 Nov. 1, 2007

(51) Int. Cl.
*B32B 27/02* (2006.01)
*B32B 27/12* (2006.01)
*B32B 27/00* (2006.01)
*B32B 5/28* (2006.01)

(52) U.S. Cl. .......... 442/118; 442/59; 442/164; 442/327

(58) Field of Classification Search ............... 442/59, 442/118, 164, 167, 301, 334, 414, 415
See application file for complete search history.

(56) References Cited

U.S. PATENT DOCUMENTS

| | | | |
|---|---|---|---|
| 4,667,890 A | 5/1987 | Gietman | |
| 4,755,421 A | 7/1988 | Manning et al. | |
| 5,540,332 A | 7/1996 | Kopacz et al. | |
| 6,562,892 B2 * | 5/2003 | Eknoian et al. | 524/457 |
| 6,602,955 B2 | 8/2003 | Soerens et al. | |
| 6,651,924 B2 | 11/2003 | Gingras et al. | |
| 6,905,748 B2 | 6/2005 | Sosalla | |
| 6,994,865 B2 | 2/2006 | Branham et al. | |
| 7,070,854 B2 | 7/2006 | Chang et al. | |
| 7,101,612 B2 | 9/2006 | Lang et al. | |
| 2003/0008591 A1 | 1/2003 | Parsons et al. | |
| 2003/0027470 A1 * | 2/2003 | Chang et al. | 442/59 |
| 2004/0055704 A1 | 3/2004 | Bunyard et al. | |
| 2004/0058600 A1 | 3/2004 | Bunyard et al. | |
| 2004/0058606 A1 | 3/2004 | Branham et al. | |
| 2004/0063888 A1 | 4/2004 | Bunyard et al. | |
| 2005/0239359 A1 | 10/2005 | Jones et al. | |

OTHER PUBLICATIONS

McCormick, "Water-Soluble Polymers", Encyclopedia of Polymer Science and Technology, online posting date Jul. 15, 2004.*
Nonwoven definition, Textile Glossary, copyright 2001, Celanese Acetate LLC.*

* cited by examiner

*Primary Examiner* — Angela Ortiz
*Assistant Examiner* — Jennifer Steele
(74) *Attorney, Agent, or Firm* — R. Joseph Foster, II

(57) ABSTRACT

A wet wipe comprises a nonwoven material. The nonwoven material comprises a fibrous material and a binder composition. The binder composition includes a cationic ion-sensitive emulsion polymer, which can comprise the emulsion polymerization product of at least one hydrophobic monomer which has been stabilized by a solution-polymerization-derived cationic ion-sensitive polymer stabilizer. In some aspects, a solution-polymerization-derived cationic ion-sensitive polymer binder can be solution blended with the already-formed cationic ion-sensitive emulsion polymer to provide additional benefits. In other aspects, the solution-polymerization-derived cationic ion-sensitive polymer binder is the same as the s-solution-polymerization-derived cationic ion-sensitive polymer stabilizer.

16 Claims, No Drawings

DISPERSIBLE WET WIPES

BACKGROUND

For many years, the problem of disposability has plagued industries that provide disposable items, such as diapers, wet wipes, incontinence garments and feminine care products. Ideally, when a disposable product is intended to be discarded in either sewer or septic systems, the product, or designated portions of the product, should "disperse" and thus sufficiently dissolve or disintegrate in water so as not to present problems under conditions typically found in either household or municipal sanitization systems. While headway has been made in addressing this problem, one of the weak links has been the inability to create economical nonwoven materials that are readily dispersible in water but still have sufficient in-use properties such as strength, thickness, opacity, absorbency, softness, flexibility, cleansing, ease-of-use, etc. to make consumer-acceptable products. These nonwoven materials may be formed by wet or dry (air) laying processes which generally provide a random plurality of fibers that are joined together adhesively and/or physically. Under appropriate conditions, some nonwoven materials can dissolve or disintegrate in water such as by simple dilution in an excess of water or dilution in excess water with the application of appropriate shear force.

U.S. patent application Ser. Nos. 10/830,558, 10/251,610, and 9/900,698 illustrate a number of approaches to forming adhesively-bonded dispersible nonwoven webs. U.S. Pat. No. 4,755,421 illustrates a variety of approaches to forming physically-bonded dispersible nonwoven fabrics, such as those formed by hydroentangling methods.

In general, ion-sensitive polymers are polymers that are insoluble in aqueous solutions containing at least about 0.3 wt % of inorganic salts but are soluble when diluted by water, such as tap water. Ion-sensitive polymers can be utilized as adhesive binders in making dispersible nonwoven and tissue-based flushable articles. Ion-sensitive polymers manufactured by solution polymerization methods known in the art, particularly in a reaction medium comprising organic solvents, are highly effective at delivering the required in-use strength and dispersibility requirements of the desired products. However, these solution polymerization processes are time-intensive and costly. Additionally, higher levels of the ion-sensitive polymers are often required to achieve the targeted in-use properties relative to the traditional crosslinking, non-dispersible binders used in current wet wipe technology. Considering these factors, the use of solution-polymerization-derived ion-sensitive polymers in flushable disposable products is cost-prohibitive despite their excellent performance properties.

In an attempt to counter the negative effects associated with solution-polymerization-derived ion-sensitive polymers, it has been found that solution blending lower-cost emulsion polymers, often referred to cobinders, with the ion-sensitive polymers can be accomplished which can allow reduced ion-sensitive polymer usage in the nonwoven material and hence reduce its cost. However, the amount of emulsion polymer cobinder that can be blended with the ion-sensitive polymers is often limited to less than 45% and more typically in the 20-35% range without resulting in significantly negative impacts to both product in-use properties and dispersibility. These negative impacts are due to generally poor bonding or interaction between the dissimilar ion-sensitive polymer and the emulsion polymer, as well as the generally more hydrophobic characteristics of emulsion polymers. Thus, the beneficial cost impact of an emulsion polymer is limited by the low amounts which can be used in the nonwoven material.

Emulsion polymerization methods offer a more cost effective approach to producing ion-sensitive polymers than solution-polymerization methods, but a generation of sufficient wet strength from emulsion-polymerization-derived ion-sensitive polymers is difficult. Such materials have been previously described as in U.S. Pat. No. 6,562,892, but materials demonstrate weak interparticle bonds, thus reducing its viability as a substitute.

Thus, there is a need for an ion-sensitive polymer which incorporates the performance advantages of a solution-polymerization-derived polymer with the cost advantages of an emulsion polymer. There is still a further need for a wet wipe that is dispersible but is cost effective.

SUMMARY

In response to the needs discussed above, a wet wipe of the present invention comprises a nonwoven material. The nonwoven material comprises a fibrous material and a binder composition. The binder composition includes a cationic ion-sensitive emulsion polymer (hereinafter referred to as "CISEP"). The CISEP can comprise the emulsion polymerization product of at least one hydrophobic monomer which has been stabilized by a solution-polymerization-derived cationic ion-sensitive polymer stabilizer. Thus, the CISEP which incorporates the beneficial properties of a "solution polymerization-derived cationic ion-sensitive polymer" (hereinafter referred to as "s-CISP") and emulsion polymerization techniques. The s-CISP stabilizer, such as those described in U.S. Patent Publication Nos. 2003/0026963 to Chang et al., 2004/0058600 to Bunyard et al. and 2004/0063888 to Bunyard et al., each of which is hereby incorporated by reference in a manner that is consistent herewith, are surface active and thus suitable for use as polymeric stabilizers. In some aspects, the CISEP comprises between 1 wt % and 55 wt % of the s-CISP stabilizer. In some particular aspects, the s-CISP stabilizer is the polymerization product of methyl acrylate and [2-(acryloxy)ethyl]trimethyl ammonium chloride.

In some aspects, the CISEP further comprises a hydrophilic monomer. In other aspects, a s-CISP binder can be solution blended with the already-formed CISEP. The s-CISP binder, such as those described in U.S. Patent Publication Nos. 2003/0026963 to Chang et al., 2004/0058600 to Bunyard et al. and 2004/0063888 to Bunyard et al., each of which is hereby incorporated by reference in a manner that is consistent herewith, are surface active and thus suitable for use as polymeric stabilizers. In other aspects, the s-CISP binder is the same as the s-CISP stabilizer. In some aspects, the CISEP comprises between 1 wt % and 55 wt % of the s-CISP binder. In some particular aspects, the s-CISP binder is the polymerization product of methyl acrylate and [2-(acryloxy)ethyl] trimethyl ammonium chloride.

The wet wipe of the present invention can be saturated with a wetting composition. In some aspects, the wetting composition comprises an aqueous solution having between about 0.3 wt % and about 10 wt % inorganic salt, such as between about 0.5 wt % and 2 wt % inorganic salt. In some features, the inorganic salt is sodium chloride. In some particular features, the sodium chloride is present in the wetting composition between 1 wt % and 2 wt %.

The wet wipe of the present invention can provide comparable performance at a reduced cost when compared to a solution blend of the s-CISP from which it is derived and an emulsion polymer of the same composition but generated using a conventional surfactant or polymer stabilization package. An improvement in wet-strength can also result for the CISEP when compared to a solution blend of the s-CISP from which it is derived and an emulsion polymer of the same composition but generated using a conventional surfactant or polymer stabilization package. In some aspects, the wet wipe of the present invention can have an in-use tensile strength of greater than 150 g/in. In other aspects, the wet wipe can have a tensile strength of less than 100 g/in after being soaked in water for 4.5 hours. In yet other aspects, the wet wipe can have a tensile strength of less than 50 g/in after being soaked in deionized water for 24 hours. In still other aspects, the wet wipe can have an in-use wet-tensile of at least 300 g/in and a tensile strength of less than 35% of the in-use wet-tensile after being soaked in deionized water for about one hour.

Numerous other features and advantages of the present invention will appear from the following description. In the description, reference is made to exemplary embodiments of the invention. Such embodiments do not represent the full scope of the invention. Reference should therefore be made to the claims herein for interpreting the full scope of the invention.

DETAILED DESCRIPTION

A wet wipe, such as a folded wet wipe, possessing improved raw materials cost is disclosed herein, wherein the wet wipe may desirably be dispersible. In one embodiment, the wet wipe may desirably be adhesively bonded with a cationic ion-sensitive emulsion polymer (herinafter referred to as "CISEP"). Such an emulsion polymer has the ability to selectively provide the wet wipe with desired in-use strength, while also providing it with the ability to lose sufficient strength such that the wet wipe will disperse when disposed in water, such as is found in toilets, for example.

The wet wipe may comprise a nonwoven material that is wetted with an aqueous solution referred to as a "wetting composition." In some aspects, the nonwoven material is a nonwoven web that comprises fibrous material and a binder composition. The binder composition of the present invention can include the CISEP of the present invention.

In some aspects, the binder composition of the present invention comprises an emulsion polymer stabilized by a solution polymerization-derived cationic ion-sensitive polymer (hereinafter referred to as "s-CISP") stabilizer. In some aspects, the binder composition further comprises a s-CISP binder that can be mixed with the already-formed CISEP. In further aspects, the s-CISP binder is the same as the s-CISP stabilizer used to form the CISEP.

The wetting composition desirably maintains the insolubility of the binder composition and may comprise an aqueous composition containing an insolubilizing agent. When the wet wipe is exposed to water, such as tap water or deionized (DI) water, the wetting composition dilutes and the binder composition desirably destabilizes. The result is a decrease in strength of the wet wipe, leading to concomitant fragmentation and dispersal of the wet wipe. Thus, the combination of the binder composition and the wetting composition can provide the structural integrity or coherency necessary to maintain the in-use strength and properties of the wet wipe, while also allowing for selective fragmentation or dispersal of the wet wipe under desired conditions.

The binder composition may be applied to the fibrous material or substrate to form the nonwoven web using a variety of techniques. In one aspect of the invention, the nonwoven web of the wet wipe may be generated by spraying the fibrous material of the web with the binder composition. However, the invention is not limited to spraying and includes other methods of applying the binder composition, as are known in the art.

Nonwoven Material

In many personal care products, nonwoven materials are the preferred substrate, especially with regard to wet wipes. Nonwoven materials may comprise either nonwoven fabrics or nonwoven webs. Nonwoven fabrics comprise fibrous material. Nonwoven webs may comprise fibrous material, such as a nonwoven fabric, and a binder composition. The nonwoven webs of the present invention comprise a fibrous material or substrate that has a structure of individual fibers or filaments randomly arranged in a mat-like fashion. Nonwoven fabrics may be made from a variety of processes including, but not limited to, airlaid processes, wet-laid processes such as with cellulosic-based tissues or towels, hydroentangling processes, staple fiber carding and bonding, and solution spinning.

The fibrous material used to form the nonwoven web may desirably have a relatively low wet cohesive strength prior to its treatment with the binder composition. Thus, when the fibrous substrate is bonded together by the binder composition, the nonwoven web will preferably break apart when it is placed in water, such as that found in toilets and sinks.

The fibers forming the fibrous material may be made from a variety of materials including natural fibers, synthetic fibers, and combinations thereof. The choice of fibers may depend upon, for example, the intended end use of the finished substrate, as well as the fiber cost. For instance, suitable fibers may include, but are not limited to, natural fibers such as cotton, linen, jute, hemp, wool, wood pulp, etc. Similarly, suitable fibers may also include, but are not limited to, regenerated cellulosic fibers, such as viscose rayon and cuprammonium rayon; modified cellulosic fibers, such as cellulose acetate; or synthetic fibers, such as those derived from polypropylenes, polyethylenes, polyolefins, polyesters, polyamides, polyacrylics, etc. Regenerated cellulose fibers, as briefly discussed above, include rayon in all its varieties as well as other fibers derived from viscose or chemically modified cellulose, including regenerated cellulose and solvent-spun cellulose, such as Lyocell.

Among wood pulp fibers, any known papermaking fibers may be used, including softwood and hardwood fibers. Fibers, for example, may be chemically pulped or mechanically pulped, bleached or unbleached, virgin or recycled, high yield or low yield, and the like. Chemically treated natural cellulosic fibers can be used, such as mercerized pulps, chemically stiffened or crosslinked fibers, or sulfonated fibers.

In addition, cellulose produced by microbes and other cellulosic derivatives can be used. As used herein, the term "cellulosic" is meant to include any material having cellulose as a major constituent, and, specifically, comprising at least 50 wt % cellulose or a cellulose derivative. Thus, the term includes cotton, typical wood pulps, non-woody cellulosic fibers, cellulose acetate, cellulose triacetate, rayon, thermo-mechanical wood pulp, chemical wood pulp, debonded chemical wood pulp, milkweed, or bacterial cellulose. Blends of one or more of any of the previously described fibers may also be used, if so desired.

The fibrous material may be formed from a single layer or multiple layers. In the case of multiple layers, the layers are generally positioned in a juxtaposed or surface-to-surface relationship and all or a portion of the layers may be bound to adjacent layers. The fibrous material may also be formed from a plurality of separate fibrous materials wherein each of the separate fibrous materials may be formed from a different type of fiber. In those instances where the fibrous material includes multiple layers, the binder composition of the present invention may be applied to the entire thickness of the fibrous material, or each individual layer may be separately treated and then combined with other layers in a juxtaposed relationship to form the finished fibrous material.

Airlaid nonwoven fabrics are particularly well suited for use as wet wipes. The basis weights for airlaid nonwoven fabrics may range from about 20 to about 200 grams per square meter (gsm) with staple fibers having a denier of about 0.5-10 and a length of about 6-15 millimeters. Wet wipes may generally have a fiber density of about 0.025 g/cc to about 0.2 g/cc. Wet wipes may generally have a basis weight of about 20 gsm to about 150 gsm, such as between about 30 to about 90 gsm or about 50 gsm to about 60 gsm.

Binder Composition

The binder composition is a component of the wet wipe which enhances cohesiveness of the fibers and/or filaments within a nonwoven web to provide in-use strength to wipe. The binder composition is desirably ion-sensitive such that in the presence of water having less than 0.3 wt % organic or inorganic salt content, it becomes soluble, thus allowing the nonwoven web to disperse. In one aspect of the invention, the binder composition can comprise the CISEP of the present invention. In another aspect, the binder composition can comprise the CISEP and a s-CISP binder. In still other aspects, the s-CISP binder is the same as a s-CISP stabilizer used to form the CISEP.

In addition to providing the wet wipe with in-use strength in the presence of a wetting composition and selective dispersibility in water, such as tap water for example, the binder composition of the present invention preferably possesses a variety of other desirable properties. For example, the binder composition can be processed on a commercial scale (i.e., the binder may be capable of rapid application on a large scale, such as by spraying) and can also desirably be less inexpensive as compared to wet wipes that utilize a s-CISP binder only, or a s-CISP/cobinder system, as discussed above. The binder composition can further provide acceptable levels of sheet wettability. In addition, it is preferred that all components of the wet wipe, including the binder composition, are desirably non-toxic and relatively economical.

In some aspects, the amount of binder composition present in the nonwoven web can range from about 5 to about 65 wt %, such as between about 7 to about 35 wt %, or between about 10 to about 25 wt % or between about 15 to about 20 wt % based on the total weight of the nonwoven web. A sufficient amount of the binder composition results in a nonwoven web that has desirable in-use integrity, but quickly disperses when soaked in water.

Cationic Ion-Sensitive Emulsion Polymer (CISEP)

The binder composition of the present invention comprises a cationic ion-sensitive emulsion polymer. This CISEP is formed by emulsion polymerization using a s-CISP as a polymeric stabilizer by means know in the art. The emulsion polymerization process used to form the CISEP may be a batch, semi-batch or continuous process.

The emulsion polymer of the CISEP is comprised of the polymerization product of at least one hydrophobic monomer and optionally one or more hydrophilic monomers. The hydrophobic monomer(s) may be selected from a wide variety of monomers, as are known in the art. For example, the hydrophobic monomer(s) may be selected from, but is not limited to, (meth)acrylates such as methyl(meth)acrylate, ethyl(meth)acrylate, butyl(meth)acrylate; (meth)acrylamides such as N-octyl (meth)acrylamide and N-butyl methacrylamide; vinyl esters such as vinyl acetate, vinyl versatate, vinyl neononanoate, vinyl neodecanoate, vinyl esters of versatic acid (VeoVA™ 10, 11, 12) vinyl-2-ethyl-hexanoate; unsaturated hydrocarbons such as ethylene, propylene, butylene, and butadiene; styrene; acrylonitrile; or combinations thereof.

The hydrophilic monomer(s) may be selected from, but is not limited to, nitrogen-functional vinyl monomers such as [2-((meth)acryloxy)ethyl]trimethyl ammonium chloride, (3-(meth)acrylamidopropyl)trimethyl ammonium chloride, N,N-diallyldimethyl ammonium chloride, dimethylaminoethyl(meth)acrylate, vinylpyridine, (meth)acrylamide, N-methyl(meth)acrylamide, N-ethyl (meth)acrylamide, N-[3-(dimethylamino)propyl](meth)acrylamide, N-vinyl formamide, N-vinyl pyrrolidone, and N-vinyl caprolactam; hydroxyl functional monomers such as hydroxyethyl(meth) acrylate, hydroxypropyl acrylate, hydroxybutyl acrylate; polyoxyalkylene functional vinyl monomers; or combinations thereof.

The total amount of the s-CISP stabilizer can be added to the reaction medium before monomer addition and emulsion polymerization or alternatively during the course of the polymerization reaction in either a continuous or a shot-feed manner. In another aspect, multiple s-CISP stabilizers can be used in the emulsion polymerization which differ in molecular weight and/or composition.

While not being bound to theory, the beneficial properties of a s-CISP as an adhesive binder for dispersible wet wipes is due to the film formation properties of such water-soluble polymers. Water-soluble polymers such as the s-CISP form entangled polymer networks upon drying into films, and these entangled polymer networks provide in-use strength to the nonwoven webs in the presence of a wetting composition (described below). Upon dilution of the wetting composition in water, the entangled polymer network of the s-CISP re-dissolves, thereby allowing strength loss and break-up of the nonwoven web. In comparison, non-chemically crosslinking emulsion polymers, which exist as stabilized water-insoluble polymer particles, require some degree of coalescence of the polymer particles upon drying to provide film strength. Under the conditions experienced during typical nonwoven web manufacturing, significant particle coalescence of such emulsion polymer particles is difficult as the timescale required for particle coalescence is typically less than 60 seconds and therefore results in weak inter-particle bonds and weak emulsion polymer films. In contrast to the above emulsion polymers, the beneficial properties achieved with the CISEP is due to incorporation of a s-CISP stabilizer into the emulsion polymer. Grafting, physical entrapment, and/or physical adsorption during the emulsion polymerization result in a greater preponderance of the s-CISP located on the surface of the emulsion polymer particles. During drying and film formation of CISEP particles, the s-CISP stabilizer located on a CISEP particle surface entangles with the s-CISP stabilizer bound to neighboring CISEP particles, thereby forming an interconnected, continuous network between the CISEP particles. The incorporated s-CISP stabilizer on the CISEP particle surface thereby imparts the ion-sensitive strength properties to the formed CISEP films. Some coalescence of the CISEP particles may occur during film formation, which is dependent upon the composition of the emulsion polymer, and thus may decrease the solubility of the CISEP films in water relative to films of the s-CISP stabilizer alone. CISEP films of the present invention either disperse in water into filterable particle aggregates or swell significantly ("ion-sensitive swelling") to form weak polymer films but do not dissolve completely as described for the s-CISP stabilizer.

The s-CISP stabilizer can be selected from a wide variety of s-CISPs known in the art. For example, s-CISPs are disclosed in the following U.S. Patent Application Publication Nos. 2004/0063888 to Bunyard et al., 2004/0055704 to Bunyard et al., 2004/0058606 to Branham et al., and 2004/0062791 to Branham et al., all of which are hereby incorporated by reference in a manner that is consistent herewith. These examples include, but are not limited to, the solution polymerization product of a vinyl-functional cationic monomer, and one or more hydrophobic vinyl monomers with alkyl side chain sizes of up to 4 carbons long. In some aspects, the ion-sensitive cationic polymers of the present invention are the solution polymerization product of a vinyl-functional cationic monomer, and one or more hydrophobic vinyl monomers with alkyl side chain sizes of up to 4 carbons long incorporated in a random manner. Additionally, a minor amount of another vinyl monomer with linear or branched alkyl groups 4 carbons or longer, alkyl hydroxy, polyoxyalkylene, or other functional groups may be employed. The s-CISP stabilizer should demonstrate insolubility in the wetting composition used to moisten the wet wipe and solubility in water, such as tap water. In one aspect, the s-CISP stabilizer is a cationic ion-sensitive polyacrylate that is the polymerization product of 96 mol % methyl acrylate and 4 mol % [2-(acryloyloxy)ethyl]trimethyl ammonium chloride.

The amount of s-CISP stabilizer present in the cationic ion-sensitive emulsion polymer can range from about 1 wt % and 55 wt %, such as between about 5 wt % and 30 wt %. In one example, the amount of s-CISP stabilizer present in the CISEP is 9 wt %. In another example, the amount of s-CISP stabilizer present in the CISEP is 10 wt %. In still another example, the amount of s-CISP stabilizer present in the stabilized CISEP is 16.5 wt %. In yet another example, the amount of s-CISP stabilizer present in the CISEP is 23 wt %. In still another example, the amount of s-CISP stabilizer present in the CISEP is 28 wt %.

In another aspect, a cosurfactant can be used in addition to the s-CISP stabilizer, such as a non-ionic surfactant or a cationic surfactant. The non-ionic surfactant is preferably an ethoxylated alcohol, of which many are commercially available and known in the art. Preferred non-ionic surfactants are non-alkylphenol-based surfactants. Example cationic surfactants include but are not limited to cetyl pyridinium chloride, and cetyl trimethylammonium chloride.

The CISEP, in addition to lowering the raw materials cost through substitution or partial substitution for the more costly s-CISP binder typically used in the binder composition for dispersible wet wipes, can provide other desirable qualities to the nonwoven web. For example, the CISEP may reduce the stiffness of the nonwoven web compared to the stiffness of a nonwoven web to which only s-CISP binder has been applied. Reduced stiffness can be achieved if the CISEP has an emulsion polymer composition with a glass transition temperature, $T_g$, that is lower than the $T_g$ of the s-CISP binder.

Solution Polymerization-Derived
Cationic Ion-Sensitive Polymer Binder (s-CISP binder)

In some aspects, the binder composition comprises a s-CISP binder that can be blended with the CISEP. A variety of s-CISP compositions can be used as a binder polymer. Examples of cationic ion-sensitive binder polymers are disclosed in the following U.S. Patent Application Publication Nos. 2004/0063888 to Bunyard et al., 2004/0055704 to Bunyard et al., 2004/0058606 to Branham et al., and 2004/0062791 to Branham et al., all of which are hereby incorporated by reference in a manner that is consistent herewith. These examples include, but are not limited to, the solution polymerization product of a vinyl-functional cationic monomer, and one or more hydrophobic vinyl monomers with alkyl side chain sizes of up to 4 carbons long. In some aspects, the s-CISP binders of the present invention are the solution polymerization product of a vinyl-functional cationic monomer, and one or more hydrophobic vinyl monomers with alkyl side chain sizes of up to 4 carbons long incorporated in a random manner.

The s-CISP binder should demonstrate insolubility in the wetting composition containing an insolubilizing agent such as an inorganic salt and solubility in water, such as tap water, for example. Additionally, a minor amount of another vinyl monomer with linear or branched alkyl groups 4 carbons or longer, alkyl hydroxy, polyoxyalkylene, or other functional groups may be employed. In one example, the s-CISP binder is a cationic polyacrylate that is the polymerization product of 96 mol % methyl acrylate and 4 mol % [2-(acryloyloxy)ethyl] trimethyl ammonium chloride.

The binder composition has a total s-CISP polymer content, which is equivalent to the total amount of s-CISP stabilizer in the CISEP and s-CISP binder. For example, in aspects where the binder composition comprises substantially CISEP, the total s-CISP content is based on the amount of s-CISP stabilizer used to form the CISEP. In aspects where the binder composition comprises a blend of CISEP and a s-CISP binder, the total s-CISP content is based on the amount of both the s-CISP stabilizer (used to form the CISEP) and s-CISP binder that are present. For example, in some aspects, the binder composition can have a total s-CISP content of between about 1 wt % and 55 wt %, such as between about 25 wt % and 70 wt %, or between about 10 wt % and 55 wt %. In one example, the binder composition has a total s-CISP content of 28 wt %. In another example, the binder composition has a total s-CISP content of 50 wt %.

In general, it may be desirable to use the highest amount of CISEP as possible in the binder composition to provide the greatest raw material cost benefit without jeopardizing the dispersibility and in-use strength properties of the wet wipe.

Wetting Composition

The wetting composition for use in combination with the nonwoven materials may desirably comprise an aqueous composition containing the insolubilizing agent that maintains the coherency of the binder composition and thus the in-use strength of the wet-wipe until the insolubilizing agent is diluted with sufficient water to provide strength loss.

Desirably, the binder composition may be insoluble in a wetting composition, wherein the wetting composition comprises at least about 0.3 weight percent of an insolubilizing agent which may be comprised of one or more inorganic and/or organic salts containing monovalent and/or divalent ions. More desirably, the binder composition may be insoluble in the wetting composition, wherein the wetting composition comprises from about 0.3% to about 10% by weight of an insolubilizing agent which may be comprised of one or more inorganic and/or organic salts containing monovalent and/or divalent ions. Even more desirably, the binder composition may be insoluble in the wetting composition, wherein the wetting composition comprises from about 0.5% to about 5% by weight of an insolubilizing agent which comprises one or more inorganic and/or organic salts containing monovalent and/or divalent ions. Especially desirably, the binder composition may be insoluble in the wetting composition, wherein the wetting composition comprises from about 1.0% to about 4.0% by weight of an insolubilizing agent which comprises one or more inorganic and/or organic salts containing monovalent and/or divalent ions.

Suitable monovalent ions include, but are not limited to, $Na^+$ ions, $K^+$ ions, $Li^+$ ions, $NH_4^+$ ions, low molecular weight quaternary ammonium compounds (e.g., those having fewer than 5 carbons on any side group), and a combination thereof. Suitable divalent ions include, but are not limited to, $Zn^{2+}$, $Ca^{2+}$ and $Mg^{2+}$. These monovalent and divalent ions may be derived from organic and inorganic salts including, but not limited to, NaCl, NaBr, KCl, $NH_4Cl$, $Na_2SO_4$, $ZnCl_2$, $CaCl_2$, $MgCl_2$, $MgSO_4$, and combinations thereof. Typically, alkali metal halides are the most desirable monovalent or divalent ions because of cost, purity, low toxicity, and availability. A particularly desirable salt is NaCl.

The wetting composition may include a variety of additives or components, including those disclosed in U.S. Patent Publication No. 2002/0155281, which is hereby incorporated by reference in a manner that is consistent herewith. Possible additives may include, but are not limited to skin-care additives, odor control additives, wetting agents and/or cleaning agents; surfactants, pH control agents, preservatives and/or anti-microbial agents.

The wet wipes, as disclosed herein, do not require organic solvents to maintain in-use strength, and the wetting composition may be substantially free of organic solvents. Organic solvents may produce a greasy after-feel and cause irritation in higher amounts. However, small amount of organic solvents may be included in the wetting composition for different purposes other than maintaining in-use wet strength. In one embodiment, small amounts of organic solvents (less than about 1%) may be utilized as fragrance or preservative solubilizers to improve process and shelf stability of the wetting composition. The wetting composition may desirably contain less than about 5 wt % of organic solvents, such as propylene glycol and other glycols, polyhydroxy alcohols, and the like, based on the total weight of the wetting composition. More desirably, the wetting composition may contain less than about 3 wt % of organic solvents. Even more desirably, the wetting composition may contain less than about 1 wt % of organic solvents.

Relative to the weight of the dry substrate, the wet wipe may desirably contain from about 10 wt % to about 600 wt % of the wetting composition, such as from about 50 wt % to about 500 wt % of the wetting composition, or from about 100 wt % to about 400 wt % of the wetting composition by weight, or from about 200 wt % to 300 wt % of the wetting composition.

Method of Making Wet Wipes

The binder composition may be applied to the fibrous material by means known in the art. Suitable processes for applying the binder composition include, but are not limited to, printing, spraying, electrostatic spraying, the use of metered press rolls and impregnating. The amount of binder composition may be metered and distributed uniformly onto the fibrous material or may be non-uniformly distributed onto the fibrous material.

For ease of application, the binder composition may be applied to the fibrous material in combination with a solvent, a solution or a mixture, with water being the preferred solvent. The amount of binder composition in the solvent may vary, depending on a variety of factors, including the identity and physical characteristics of the CISEP and optional s-CISP binder that is being used, as well as the identity and physical characteristics of the fibrous material to which the binder composition is being applied. Desirably, the mixture or solution of the binder composition may contain up to about 50 wt % of binder composition solids, such as from about 10 wt % to 30 wt % or about 12 wt % to 25 wt % binder composition solids.

Once the binder composition is applied to the fibrous material, drying, if necessary, may be achieved by any conventional means known in the art. Once dry, the nonwoven material may exhibit improved tensile strength when compared to the tensile strength of the untreated fibrous material, and yet should have the ability to rapidly "fall apart" or disintegrate when placed in water.

A number of techniques may be employed to manufacture the wet wipes. In one embodiment, these techniques may include the following steps:

1. Providing the fibrous material (e.g., an unbonded airlaid, a tissue web, a carded web, fluff pulp, etc.).
2. Applying the binder composition to the fibrous material, typically in the form of a liquid, suspension, or foam to form the nonwoven web.
3. Drying the nonwoven web.
4. Applying a wetting composition to the nonwoven web to generate the wet wipe.
5. Placing the wet wipe in roll form or in a stack and packaging the product.

Wipes may also be prepared by applying the binder composition to the fibrous material, followed by drying and winding of the resulting nonwoven web into a roll. In this aspect, the wetting composition may be added some time later. For example, large rolls of the dry nonwoven web may be prepared as an intermediate material. This procedure may be advantageous as part of the manufacturing process.

The finished wet wipes may be individually packaged, desirably in a folded condition, in a moisture proof envelope or packaged in containers holding any desired number of sheets in a water-tight package with a wetting composition applied to the wipe. The wet wipes can be stacked in a container in either a folded or unfolded configuration. For example, containers of wet wipes are available wherein each of the wet wipes are arranged in a folded configuration including, but not limited to, c-folded, z-folded, or quarter-folded configurations as are well known to those skilled in the art. Sometimes the folded wet wipes are also interfolded with the wet wipes immediately above and below in the stack of wet wipes. In yet other configurations, the wet wipes can be placed in the container in the form of a continuous nonwoven material. In this case, each individual wet wipe or sheet may be connected, from the first sheet to the last, by similarly weakened lines of perforations or by adhesive bonds. These wet wipes can be stacked on top of each other in a fan folded manner or can be wound into a roll configuration. Some example processes which can be used to manufacture folded wet wipes are described in U.S. Pat. Nos. 5,540,332 to Kopacz et al. and 6,905,748 to Sosalla, which are hereby incorporated by reference in a manner that is consistent herewith. The finished wipes may also be packaged as a roll of separable sheets in a moisture-proof container holding any desired number of sheets on the roll with a wetting composition applied to the wipes. The roll can be coreless and either hollow or solid. Coreless rolls, including rolls with a hollow center or without a solid center, can be produced with known coreless roll winders, including those of SRP Industry, Inc. (having a place of business located in San Jose, Calif., U.S.A.); Shimizu Manufacturing (having a place of business located in Japan), and the devices disclosed in U.S. Pat. No. 4,667,890 to Geitman, Jr. which is hereby incorporated by reference in a manner that is consistent herewith. U.S. Pat. No. 6,651,924 Gingras et al. also provides examples of a process for producing coreless rolls of wet wipes, which is hereby incorporated by reference in a manner that is consistent herewith.

Wet Wipe Properties

The wet wipes, as disclosed herein, desirably may be made to have sufficient in-use wet tensile strength, wet thickness, opacity, and dispersibility. They may also be made to be usable without breaking or tearing when in use, to be consumer acceptable, and to provide problem-free disposal once disposed in a household sanitation system.

The wet wipe as disclosed herein desirably may have an in-use wet strength ranging from at least about 100 g/in to about 1000 g/in., such as between about 200 g/in to about 800 g/in., or between about 300 g/in to about 600 g/in. or between about 350 g/in to about 550 g/in.

The wet wipe may be configured to provide all desired physical properties by use of a single or multi-ply wet wipe product, in which two or more plies of nonwoven material are joined together by methods known in the art to form a multi-ply wipe.

The total basis weight of the nonwoven material, consisting of a single or multiple layers of nonwoven material in the final wet wipe product, may be in the range of at least about 25 gsm to about 1.20 gsm, such as between about 40 gsm and 90 gsm, or between about 60 gsm and 80 gsm or between about 70 and 75 gsm.

The wet opacity of the wet wipe, or the tendency of the wet wipe to prevent the transmission of light, may desirably be higher (i.e. less transmitted light) as it provides an indication that the wet wipe will be able to perform its desired function without breaking or tearing. Desirably, the wet wipe, as disclosed herein, may have a wet opacity greater than about 20%, such as greater than about 35% or greater than about 45%.

The average thickness of the wet wipe may be in the range of at least about 0.25 mm to about 1.5 mm, such as between 0.3 mm and 1.0 mm or between 0.5 mm and 1.0 mm.

As mentioned previously, the wet wipes, as disclosed herein, may be sufficiently dispersible so that they lose enough strength to break apart in tap water under conditions typically experienced in household or municipal sanitation systems. Previous methods for measuring dispersibility of the nonwoven materials whether dry or pre-moistened, have commonly relied on systems in which the material was exposed to shear while in water, such as measuring the time for a material to break up while being agitated by a mechanical mixer. Constant exposure to such relatively high, uncontrolled shear gradients offers an unrealistic and overly optimistic test for products designed to be flushed in a toilet, where the level of shear is extremely weak or brief. Shear rates may be negligible, for example once the material enters a septic tank. Thus, for a realistic appraisal of wet wipe dispersibility, the test methods should simulate the relatively low shear rates the products will experience once they have been flushed in the toilet.

A static soak test, for example, should illustrate the dispersibility of the wet wipe after it is fully wetted with water from the toilet and where it experiences negligible shear, such as in a septic tank. Desirably, the wet wipe may have less than about 100 g/in of tensile strength after 5 h when soaked in water with a total dissolved solids up to 500 ppm and a $CaCO_3$ equivalent hardness up to about 250 ppm. More desirably, the wet wipe may have less than about 100 g/in of tensile strength after 3 h when soaked in water with a total dissolved solids up to 500 ppm and a $CaCO_3$ equivalent hardness up to about 250 ppm. Even more desirably, the wet wipe may have less than about 100 g/in of tensile strength after 1 h when soaked in water with a total dissolved solids up to 500 ppm and a $CaCO_3$ equivalent hardness up to about 250 ppm.

Desirably, the wet wipes, as disclosed herein, may possess an in-use wet tensile strength of at least about 150 g/in when wetted with 10% to 400% of the wetting composition by weight relative to the weight of the nonwoven material, and a tensile strength of less than about 100 g/in when soaked in water with a total dissolved solids up to 500 ppm and a $CaCO_3$ equivalent hardness up to about 250 ppm after about 24 hours or less, desirably after about one hour.

Most desirably, the wet wipes, as disclosed herein, may possess an in-use wet tensile strength greater than about 300 g/in when wetted with 10% to 400% of the wetting composition by weight relative to the nonwoven material, and a tensile strength of less than about 100 g/in when soaked in water with a total dissolved solids up to 500 ppm and a $CaCO_3$ equivalent hardness up to about 250 ppm after about 24 hours or less, desirably after about one hour.

The wet wipe preferably maintains its desired characteristics over the time periods involved in warehousing, transportation, retail display and storage by the consumer. In one embodiment, shelf life may range from two months to two years.

EXAMPLES

Materials

The reagents methyl acrylate, vinyl acetate, N-vinyl caprolactam, 2,2'-azobis(2-methylpropionamidine)dihydrochloride, and dodecyl mercaptan were all obtained from Sigma-Aldrich Corp. (having a place of business located in St. Louis, Mo., U.S.A.). The cationic ion-sensitive polyacrylate described in the following examples is a copolymer of methyl acrylate (96 mol %) and [(2-acryloyloxy)ethyl]trimethyl ammonium chloride (4 mol %) with a weight average molecular weight between 140,000 to 200,000 g/mol as determined by gel permeation chromatography in a dimethylformamide/LiCl mobile phase. The cationic ion-sensitive polyacrylate used in the experiments was synthesized by solution polymerization methods in a 75/25 acetone/water mixture and then solvent exchanged to an approximately 23 wt % aqueous solution by distillation methods. Unless otherwise stated, the cationic ion-sensitive polyacrylate was utilized as both the s-CISP stabilizer and the s-CISP binder.

Lab-Preparation of Airlaid Nonwoven Web Basesheets

A weak, 50 gsm, 1.0 mm thick thermally-bonded airlaid fibrous material was cut into 25.4 cm×33.0 cm handsheets. The airlaid had a residual wet tensile strength of 30 g/in. This thermally-bonded airlaid material was prepared as described in U.S. Patent Application Publication No. 2004/0063888 to Bunyard et al., which is hereby incorporated by reference in a manner that is consistent herewith. Using the binder compositions described herein, the thermally-bonded airlaid handsheets were treated with a 15 wt % mixture of the binder composition using a pressurized spray unit to achieve a final 24 wt % total content of binder composition in the handsheets. The resulting lab-prepared airlaid nonwoven webs were then manually removed and dried in a WERNER MATHIS, Model LTV Through-Air Dryer (TAD) at 180° C. for 23 seconds at 100% fan speed.

Lab-Prepared Wet Wipe Preparation and Aging Protocol

Each 25.4 cm×33.0 cm lab-prepared airlaid nonwoven web was die cut into two 19.1 cm×14.0 cm dry wipes, with the shorter direction being the machine-direction (MD). Each dry wipe was then sprayed with a 250 wt % add-on of a wetting composition comprising 2 wt % sodium chloride (insolubilizing agent) to yield lab-prepared wet wipes. A stack of 6 lab-prepared wet wipes was formed and placed inside a re-sealable plastic bag. The stack of 6 lab-prepared wet wipes in the re-sealable plastic bag was compressed using an ATLAS laboratory wringer (available from Atlas Electric Devices Company, having a place of business in Chicago, Ill., U.S.A.)

with no additional load added. The compressed stack of thermally-bonded airlaid wet wipes was then aged under 1000 grams of weight for 72 hours.

Wet-Wipe Tensile Measurements

A SINTECH 1/D tensile tester with TESTWORKS 4.08 version software (or equivalent tensile tester), and a 100 Newton load cell with pneumatic grips was utilized for all sample testing. After removal from the re-sealable plastic bag, the wet wipes were cut in the center in the MD direction to form a stack of 2.5 cm×14.0 cm wet-wipe strips, 6 layers thick.

Wet-Wipe In-Use Tensile Strength Measurements

In-use wet tensile and residual soak tensile measurements were determined using a pneumatic grip gauge separation of 5.1 cm and a crosshead speed of 30.1 cm/min. The peak load values (g/cm) of at least 6 sample replicates were recorded and averaged and reported as machine-direction wet tensile strength (MDWT) or cross-deckle wet tensile strength (CDWT). The results can be seen in the tables below.

Wet-Wipe Dispersibility—Soak Measurements

Dispersibility of the wet wipes was gauged by soaking the wet wipe strips in a defined volume of an aqueous solution. The volume (mL) of the aqueous solution was adjusted to equal 410 mL per wet wipe strips. For example, 12 wet wipe strips would require 4920 mL of aqueous test solution. Six sample replicates were used for each tensile measurement. The wet wipe strips were soaked in the aqueous test solution for set periods of time (1, 4.5, and 24 hours) before residual soak strength measurements were recorded using the tensile method described above. Deionized water was utilized as the test solution for dispersibility measurements. Soaking the test strips in an excess of deionized water provided a measure of whether the binder composition was capable of providing a tensile loss with time without the additional influence of tap water ions.

Ion-Sensitive Solubility Determination

Films were cast and air-dried from the CISEP described in Examples 1-7 below. Approximately 1.0 gram of dried film was placed in a sealed 20 mL vial containing either a 4 wt % NaCl solution or deionized water. The vials were placed on an oscillating shaker for 24 hours and monitored for changes in appearance.

Example 1

A quantity of 350 grams of deionized water and 70 grams of a 23.1% solution of cationic ion-sensitive polyacrylate (s-CISP stabilizer) were added to a 1-L cylindrical, water-jacketed glass reactor equipped with a condenser, thermocouple, and TEFLON paddle agitator. The reaction mixture was heated to 80° C. while purging with a gentle stream of nitrogen for at least 15 minutes and stirring at 200 revolutions per minute (rpm). Then, an initiator solution was formed by dissolving 0.47 grams of 2,2'-azobis(2-methylpropionamidine)dihydrochloride in 4.53 grams of deionized water. Once the reaction mixture reached a temperature of 80° C., 150 grams of vinyl acetate and the initiator solution were simultaneously pumped into the reaction mixture through separate inlets over 3 hours and 3.5 hours respectively. After the monomer and initiator solutions were added to the reaction mixture, the reaction mixture was held for an additional 1.5 hours. The resulting stabilized cationic ion-sensitive emulsion polymer (CISEP) was approximately 29 wt % solids with approximately 10 wt % of the solids consisting of the cationic ion-sensitive polyacrylate. The cast film remained insoluble, clear and strong with no change in appearance or dimensions in 4% NaCl solution. In deionized (DI) water, the cast film remained insoluble but became translucent and weaker while remaining intact over 24 hours.

Example 2

A quantity of 350 grams of deionized water and 65 grams of a 23.1% solution of cationic ion-sensitive polyacrylate (s-CISP stabilizer) were added to a 1-L cylindrical, water-jacketed glass reactor equipped with a condenser, thermocouple, and TEFLON paddle agitator. The reaction mixture was heated to 80° C. while purging with a gentle stream of nitrogen for at least 15 minutes and stirring at 200 rpm. Then, an initiator solution was formed by dissolving 0.47 grams of 2,2'-azobis(2-methylpropionamidine)dihydrochloride in 4.53 grams of deionized water. Once the reaction mixture reached a temperature of 80° C., 150 grams of methyl acrylate and the initiator solution were simultaneously pumped into the reaction mixture through separate inlets over 3 hours and 3.5 hours respectively. After the monomer and initiator solutions were added to the reaction mixture, the reaction mixture was held for an additional 1.5 hours. The resulting stabilized cationic ion-sensitive emulsion polymer (CISEP) was approximately 29 wt % solids with approximately 10 wt % of the solids consisting of the cationic ion-sensitive polyacrylate. The cast film remained insoluble, clear and strong with no change in appearance or dimensions in 4% NaCl solution. In DI water, the cast film swelled significantly and became opaque and weaker while remaining intact over 24 hours.

Example 3

A quantity of 335 grams of deionized water and 130 grams of a 23.1% solution of cationic ion-sensitive polyacrylate (s-CISP stabilizer) were added to a 1-L cylindrical, water-jacketed glass reactor equipped with a condenser, thermocouple, and TEFLON paddle agitator. The reaction mixture was heated to 80° C. while purging with a gentle stream of nitrogen for at least 15 minutes and stirring at 200 rpm. Then, an initiator solution was formed by dissolving 0.47 grams of 2,2'-azobis(2-methylpropionamidine)dihydrochloride in 4.53 grams of deionized water. Once the reaction mixture reached a temperature of 80° C., a monomer solution of 152 g of vinyl acetate and the initiator solution were simultaneously pumped into the reaction mixture through separate inlets over 3 hours and 3.5 hours respectively. After the monomer and initiator solutions were added to the reaction mixture, the reaction mixture was held for an additional 1.5 hours. The resulting cationic ion-sensitive emulsion polymer (CISEP) was approximately 29 wt % solids with approximately 16.5 wt % of the solids consisting of the cationic ion-sensitive polyacrylate. The cast film remained insoluble, clear and strong with no change in appearance or dimensions in 4% NaCl solution. In DI water, the cast film swelled significantly and became translucent and weaker while remaining intact over 24 hours.

Example 4

A quantity of 325 grams of deionized water and 196 grams of a 23.1% solution of cationic ion-sensitive polyacrylate (s-CISP stabilizer) were added to a 1-L cylindrical, water-jacketed glass reactor equipped with a condenser, thermocouple, and TEFLON paddle agitator. The reaction mixture was heated to 60° C. while purging with a gentle stream of nitrogen for at least 15 minutes and stirring at 200 rpm. Then, an initiator solution was formed by dissolving 0.47 grams of 2,2'-azobis(2-methylpropionamidine)dihydrochloride in 4.53 grams of deionized water. Once the reaction mixture reached a temperature of 60° C., the monomer solution of 152 g of vinyl acetate and the initiator solution were simultaneously pumped into the reaction mixture through separate inlets over 3 hours and 3.5 hours respectively. After the monomer and initiator solutions were added to the reaction mixture, the reaction mixture was held for an additional 1.5 hours. The resulting cationic ion-sensitive emulsion polymer (CISEP) was approximately 29 wt % solids with approximately 23 wt % of the solids consisting of the cationic ion-sensitive polyacrylate. The cast film remained insoluble, clear and strong with no change in appearance or dimensions in 4% NaCl solution. In DI water, the cast film swelled significantly and became translucent and weaker while remaining intact over 24 hours.

Example 5

A quantity of 310 grams of deionized water and 260 grams of a 23.1% solution of cationic ion-sensitive polyacrylate (s-CISP stabilizer) were added to a 1-L cylindrical, water-jacketed glass reactor equipped with a condenser, thermocouple, and TEFLON paddle agitator. The reaction mixture was heated to 60° C. while purging with a gentle stream of nitrogen for at least 15 minutes and stirring at 200 rpm. Then, an initiator solution was formed by dissolving 0.47 grams of 2,2'-azobis(2-methylpropionamidine)dihydrochloride in 4.53 grams of deionized water. Once the reaction mixture reached a temperature of 60° C., a monomer solution of 153 g of vinyl acetate and the initiator solution were simultaneously pumped into the reaction mixture through separate inlets over 3 hours and 3.5 hours respectively. After the monomer and initiator solutions were added to the reaction mixture, the reaction mixture was held for an additional 1.5 hours. The resulting stabilized cationic ion-sensitive emulsion polymer (CISEP) was approximately 28 wt % solids with approximately 23 wt % of the solids consisting of the cationic ion-sensitive polyacrylate. The cast film remained insoluble, clear and strong with no change in appearance or dimensions in 4% NaCl solution. In DI water, the cast film swelled significantly and became translucent and weaker while remaining intact over 24 hours.

Example 6

A quantity of 311 grams of deionized water and 259 grams of a 23.1% solution of cationic ion-sensitive polyacrylate (s-CISP stabilizer) were added to a 1-L cylindrical, water-jacketed glass reactor equipped with a condenser, thermocouple, and TEFLON paddle agitator. The reaction mixture was heated to 60° C. while purging with a gentle stream of nitrogen for at least 15 minutes and stirring at 216 rpm. Next, a monomer solution was created by mixing 113 gram of vinyl acetate and 39 grams of N-vinylcaprolactam to form a solution. Then, an initiator solution was formed by dissolving 0.43 grams of 2,2'-azobis(2-methylpropionamidine) dihydrochloride in 4.53 grams of deionized water. Once the reaction mixture reached a temperature of 60° C., the monomer solution and the initiator solution were simultaneously pumped into the reaction mixture through separate inlets over 3 hours and 3.5 hours respectively. After the monomer and initiator solutions were added to the reaction mixture, the reaction mixture was held for an additional 1.5 hours. The resulting cationic ion-sensitive emulsion polymer (CISEP) was approximately 29 wt % solids with approximately 28 wt % of the solids consisting of the cationic ion-sensitive polyacrylate. The cast film remained insoluble, became opaque but remained strong in 4% NaCl solution. In DI water, the cast film broke up into a milky, white dispersion.

Example 7

A quantity of 313 grams of deionized water and 260 grams of a 23.1% solution of cationic ion-sensitive polyacrylate (s-CISP stabilizer) were added to a 1-L cylindrical, water-jacketed glass reactor equipped with a condenser, thermocouple, and TEFLON paddle agitator. The reaction mixture was heated to 60° C. while purging with a gentle stream of nitrogen for at least 15 minutes and stirring at 216 rpm. Next, a monomer solution was created by mixing 155 grams of methyl acrylate and 0.15 grams of dodecyl mercaptan to form a solution. Then, an initiator solution was formed by dissolving 0.43 grams of 2,2'-azobis(2-methylpropionamidine) dihydrochloride in 4.53 grams of deionized water. Once the reaction mixture reached a temperature of 60° C., the monomer solution and initiator solution were simultaneously pumped into the reaction mixture through separate inlets over 3 hours and 3.5 hours respectively. After the monomer and initiator solutions were added to the reaction mixture, the reaction mixture was held for an additional 1.5 hours. The resulting cationic ion-sensitive emulsion polymer (CISEP) was approximately 29 wt % solids with approximately 28 wt % of the solids consisting of the cationic ion-sensitive polyacrylate. The cast film remained insoluble, clear and strong with no change in appearance or dimensions in 4% NaCl solution. In DI water, the cast film swelled significantly and became translucent and weaker while remaining intact over 24 hours.

The emulsion polymers described in examples 5, 6, 7 were used in binder compositions of airlaid nonwoven webs, wherein the binder compositions consisted of either 1) the CISEP alone or 2) a mixture of the CISEP with a s-CISP binder, as described in Table 1 below. Wet strength values were obtained with a wetting composition containing 2 wt % NaCl. Upon soaking each wet wipe in an excess of deionized water, a residual soak strength was obtained after 1 hour, 4.5 hours, and 24 hours. Tensile performance of lab-prepared wet wipes derived from these airlaid nonwoven webs are discussed below and are provided in Table 1.

Comparative Example A in Table 1 consisted of the cationic ion-sensitive polyacrylate (the s-CISP binder) as the sole component of the binder composition in the wet wipe. A high in-use wet strength was obtained with a wetting composition containing 2 wt % NaCl. Upon soaking the wet wipe in an excess of deionized water, a residual soak strength lower than the in-use strength was obtained after 1 hour, which decreased further after 4.5 hours, and decreased still further after 24 hours.

Binder Composition B consisted of the CISEP of the present invention described in Example 5. The CISEP of Example 5 comprised 28 wt % cationic ion-sensitive polyacrylate (the s-CISP stabilizer) and 72 wt % poly(vinyl acetate). A wet wipe comprising Binder Composition B exhibited a high in-use wet strength (>400 g/in), thereby demonstrating good bonding of the nonwoven web by the CISEP. The residual soak strength decreased after 1 hour to 85% of the in-use wet strength, and then decreased by an additional 5% after 24 hours.

Binder Composition C consisted of a blend of 70 wt % of the CISEP of Example 5 and 30 wt % cationic ion-sensitive polyacrylate (the s-CISP binder), wherein the total cationic ion-sensitive polyacrylate content (i.e., s-CISP binder and s-CISP stabilizer) was 50 wt %. A wet wipe comprising Binder Composition C demonstrated good bonding of the nonwoven web by virtue of a high in-use wet strength (>400 g/in) as compared to Binder Composition B, and exhibited improved residual soak strengths after 4.5 hours and 24 hours as compared to Binder Composition B. Blending of the cationic ion-sensitive polyacrylate binder with the CISEP improved the dispersibility of the binder composition.

Binder Composition D consisted of the CISEP described in Example 6. The CISEP of Example 6 comprised 28 wt % cationic ion-sensitive polyacrylate and 72 wt % of a vinyl acetate/N-vinylcaprolactam copolymer. A wet wipe comprising Binder Composition D demonstrated good bonding of the nonwoven web with an in-use wet strength of approximately 280 g/in. The residual soak strengths were improved over Binder Compositions B and C, with the residual soaks dropping to less than 28% of the in-use wet strength after 4.5 hours. Incorporation of the hydrophilic monomer N-vinylcaprolactam into the emulsion polymer appears to have improved the dispersibility of the binder composition. This also demonstrates that a CISEP which disperses in water to filterable particle aggregates can be used as a primary binder component in a binder composition to generate a dispersible wet wipe.

Binder Composition E consisted of a blend of 70 wt % of the CISEP of Example 6 and 30 wt % cationic ion-sensitive polyacrylate binder polymer, wherein the total cationic ion-sensitive polyacrylate content was 50 wt %. A wet wipe comprising Binder Composition E demonstrated improved bonding of the nonwoven web as compared to Binder Composition D as indicated by the increase of in-use wet strength from approximately 280 g/in to approximately 420 g/in. The dispersibility of Binder Composition E was improved over that of Binder Composition D, as indicated by a drop in the residual soak strength to less than 12% of the initial wet strength for Composition E after 4.5 hours, compared to a drop to less than 28% for Composition D after 4.5 hours.

Binder Composition F consisted of the CISEP described in Example 7. The CISEP of Example 7 comprised 28 wt % cationic ion-sensitive polyacrylate and 72 wt % of poly(methyl acrylate). A wet wipe comprising Binder Composition F demonstrated good bonding of the nonwoven web with a high in-use wet strength (>400 g/in). A drop in the residual soak strengths to 72% of the in-use strength was achieved after 24 hours.

Binder Composition G consisted of a blend of 70 wt % CISEP of Example 7 and 30 wt % cationic ion-sensitive polyacrylate binder polymer, wherein the total cationic ion-sensitive polyacrylate content in the binder composition was 50 wt %. The wet wipe of Binder Composition G demonstrated comparable in-use wet strength to that of Binder Composition F (>400 g/in.). However, improved dispersibility was obtained in Binder Composition G as compared to Binder Composition F as indicated by decreased residual soak strength of Binder Composition G to 5% of the in-use wet strength after 24 hours. Increasing the total cationic ion-sensitive polyacrylate content in the binder composition significantly improved the dispersibility of the binder composition while still only comprising of 50 wt % of the cationic ion-sensitive polyacrylate. This demonstrates that a CISEP which does not disperse in water to filterable particle aggregates but rather only shows ion-sensitive swelling and water absorption can be used in a binder composition to generate a dispersible wet wipe.

The results are summarized in Table 1 below.

TABLE 1

| Binder Composition | CISEP example in Binder Composition | CISEP in Binder Composition (wt %) | Total Cationic Ion-Sensitive Polyacrylate Content in Binder Composition (wt %) | Machine-Direction Wet Tensile Strength (g/in) | | | |
|---|---|---|---|---|---|---|---|
| | | | | In-Use Wet Strength | Residual Soak Wet Strength (1 h) | Residual Soak Wet Strength (4.5 h) | Residual Soak Wet Strength (24 h) |
| A | none | 0 | 100 | 428 | 100 (23)* | 37 (9)* | 10 (2)* |
| B | 5 | 100 | 28 | 455 | 385 (85)* | 355 (78)* | 363 (80)* |
| C | 5 | 70 | 50 | 427 | 322 (75)* | 258 (60)* | 199 (47)* |
| D | 6 | 100 | 28 | 283 | 153 (54)* | 78 (28)* | 95 (34)* |
| E | 6 | 70 | 50 | 423 | 143 (34)* | 51 (12)* | 37 (9)* |
| F | 7 | 100 | 28 | 424 | 324 (76)* | 310 (73)* | 307 (72)* |
| G | 7 | 70 | 50 | 431 | 227 (53)* | 155 (36)* | 23 (5)* |

*The parenthetical represents the percentage strength remaining as compared to the initial in-use wet strength. For instance, using Example A, the Residual Soak Wet Strength after 1 hour soak time in deionized water was 100 grams/inch, which represents 23% of the initial 428 g/in In-Use Wet Strength.

The previous examples utilized binder compositions in which the CISEP partially comprised the cationic ion-sensitive polyacrylate. Use of a cobinder not comprising the s-CISP stabilizer requires a higher content of the cationic ion-sensitive polyacrylate binder in the binder composition to maintain sufficient in-use wet strength and dispersibility. This is illustrated in Table 2 below where binder compositions I and J comprise mixtures of a cationic ion-sensitive polyacrylate binder and RESYN-225A, which is a cationic poly(vinyl acetate) emulsion latex available from National Starch and Chemical Company (having a place of business located in Bridgewater, N.J., U.S.A.). RESYN-225A is not stabilized with a s-CISP stabilizer, but rather is stabilized with a conventional surfactant package. As can be seen in Table 2, decreasing the amount of the cationic ion-sensitive polyacrylate from 100 wt % in the binder composition to 65 wt % results in a decrease of the in-use wet strength by 22%. Binder Composition K, which is composed of only the cobinder emulsion polymer demonstrates significantly lower in-use wet strength thereby illustrating the poor bonding of the poly(vinyl acetate) emulsion polymer particles under the nonwoven processing conditions and poor dispersibility as indicated by the >89% wet-strength retention after soaking. In contrast, the binder compositions of Example B and Example C, which also contained poly(vinyl acetate) but were stabilized with a s-CISP stabilizer, maintained comparable in-use wet strength to that of the binder composition of Comparative Example A with only 28 wt % and 50 wt % cationic ion-sensitive polyacrylate content, respectively. Thus, the wet wipes of the invention demonstrate comparable performance to wet wipes having a s-CISP binder only and at a reduced cost, based on binder composition components.

TABLE 2

| Binder Composition | Cationic Ion-Sensitive Polyacrylate Content in Binder Composition (wt %) | RESYN 225-A Content in Binder Composition (wt %) | Machine-Direction Wet Tensile (g/in) | | |
|---|---|---|---|---|---|
| | | | In-Use Strength | Residual Soak Strength (1 h) | Residual Soak Strength (3 h) |
| H | 100 | 0 | 430 | 111 (26)* | 92 (21)* |
| I | 75 | 25 | 359 | 126 (35)* | 98 (27)* |
| J | 65 | 35 | 334 | 148 (44)* | 112 (34)* |
| K | 0 | 100 | 117 | 104 (89)* | 106 (91)* |

*The parenthetical represents the percentage strength remaining as compared to the initial in-use wet strength. For instance, using Example H, the Residual Soak Wet Strength after 1 hour soak time in deionized water was 111 grams/inch, which represents 26% of the initial 428 g/in In-Use Wet Strength.

It will be appreciated that details of the foregoing examples, given for purposes of illustration, are not to be construed as limiting the scope of this invention. Although only a few exemplary embodiments of this invention have been described in detail above, those skilled in the art will readily appreciate that many modifications are possible in the examples without materially departing from the novel teachings and advantages of this invention. For example, features described in relation to one example may be incorporated into any other example of the invention.

Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention. As various changes could be made in the above constructions without departing from the scope of the invention, it is intended that all matter contained in the above description shall be interpreted as illustrative and not in a limiting sense.

What is claimed is:

1. A wet wipe comprising a nonwoven material;
wherein the nonwoven material comprises a binder composition;
wherein the binder composition comprises a cationic ion-sensitive emulsion polymer;
wherein the cationic ion-sensitive emulsion polymer comprises the emulsion polymerization product of at least one hydrophobic monomer which has been stabilized by a solution-polymerization-derived cationic ion-sensitive polymer stabilizer;
wherein the cationic ion-sensitive emulsion polymer comprises between 1 wt % and 55 wt % of the solution-polymerization-derived cationic ion-sensitive polymer stabilizer;
wherein the nonwoven material comprises a fibrous material; and
wherein the solution-polymerization-derived cationic ion-sensitive polymer stabilizer is the polymerization product of methyl acrylate and [2 (acryloxy)ethyl]trimethyl ammonium chloride.

2. The wet wipe of claim 1 wherein the hydrophobic monomer is selected from (meth)acrylates such as methyl(meth)acrylate, ethyl(meth)acrylate, butyl (meth)acrylate; (meth)acrylamides such as N-octyl(meth)acrylamide and N-butyl methacrylamide; vinyl esters such as vinyl acetate, vinyl versetate, vinyl neononanoate, vinyl neodecanoate, vinyl esters of versatic acid; unsaturated hydrocarbons such as ethylene, propylene, butylene, and butadiene; styrene; acrylonitrile; or combinations thereof.

3. The wet wipe of claim 1, wherein the cationic ion-sensitive emulsion polymer further comprises a hydrophilic monomer.

4. The wet wipe of claim 1 wherein the binder composition further comprises a solution-polymerization-derived cationic ion-sensitive polymer binder.

5. The wet wipe of claim 4 wherein the solution-polymerization-derived cationic ion-sensitive polymer binder is the same as the solution-polymerization-derived cationic ion-sensitive polymer stabilizer.

6. The wet wipe of claim 4 wherein the binder composition has a total solution polymerization-derived cationic ion-sensitive polymer content between 1 wt % and 55 wt %.

7. The wet wipe of claim 1 wherein the solution polymerization-derived cationic ion-sensitive polymer binder is the polymerization product of methyl acrylate and [2 (acryloxy)ethyl]trimethyl ammonium chloride.

8. The wet wipe of claim 1 wherein the wet wipe is saturated with a wetting composition.

9. The wet wipe of claim 8 wherein the wetting composition comprises an aqueous solution having between 0.3 wt % and 10 wt % inorganic salt.

10. The wet wipe of claim 9 wherein the wetting composition comprises an aqueous solution having between 0.5 wt % and 2 wt % inorganic salt.

11. The wet wipe of claim 9 wherein the inorganic salt is sodium chloride.

12. The wet wipe of claim 11 wherein the sodium chloride is present in the wetting composition between 1 wt % and 2 wt %.

13. The wet wipe of claim 1 having an in-use tensile strength of greater than 150 g/in.

14. The wet wipe of claim 1 having a tensile strength of less than 100 g/in after being soaked in for 4.5 hours in deionized water.

15. The wet wipe of claim 1 having a tensile strength of less than 50 g/in after being soaked in deionized water for 24 hours.

16. The wet wipe of claim 1 having an in-use wet-tensile of at least 300 g/in and a tensile strength of less than 35% of the in-use wet-tensile after being soaked in deionized water for about one hour.

* * * * *